United States Patent
Perrey et al.

(10) Patent No.: US 9,947,097 B2
(45) Date of Patent: Apr. 17, 2018

(54) METHOD AND SYSTEM FOR ENHANCED FETAL VISUALIZATION BY DETECTING AND DISPLAYING A FETAL HEAD POSITION WITH CROSS-PLANE ULTRASOUND IMAGES

(71) Applicant: General Electric Company, Schenectady, NY (US)

(72) Inventors: Christian Fritz Perrey, Zipf (AT); Klaus Pintoffl, Zipf (AT); Walter Duda, Jr., Zipf (AT); Lucienne van der Veen, Vienna (AT)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 101 days.

(21) Appl. No.: 15/000,221

(22) Filed: Jan. 19, 2016

(65) Prior Publication Data
US 2017/0206659 A1 Jul. 20, 2017

(51) Int. Cl.
*G06T 7/00* (2017.01)
*A61B 8/00* (2006.01)
(Continued)

(52) U.S. Cl.
CPC .......... *G06T 7/0046* (2013.01); *A61B 8/0866* (2013.01); *A61B 8/13* (2013.01);
(Continued)

(58) Field of Classification Search
None
See application file for complete search history.

(56) References Cited

U.S. PATENT DOCUMENTS

| 6,669,653 B2 * | 12/2003 | Paltieli | A61B 17/42 600/588 |
| 7,850,625 B2 * | 12/2010 | Paltieli | A61B 5/061 128/916 |

(Continued)

OTHER PUBLICATIONS

Casciaro et al., "Quantitative and Automatic Echographic Monitoring of Labor Progression," IEEE Int. Ultrasonics Symposium, Dresden, Germany, Oct. 7-10, 2012.*

(Continued)

*Primary Examiner* — Matthew Bella
*Assistant Examiner* — Soo Shin
(74) *Attorney, Agent, or Firm* — McAndrews, Held & Malloy, Ltd.; Jacob Groethe; David Bates

(57) ABSTRACT

A processor identifies a first set of characteristic models of a structure in cross-plane images acquired at a first acquisition period. The processor identifies a second set of characteristic models of the structure in cross-plane images acquired at a second subsequent acquisition period. The processor determines an amount of rotation of the structure based at least in part on a difference in shape of the first set of characteristic models and the second set of characteristic models. The system and method may include determining a labor progress based at least in part on the determined amount of rotation of the structure. The structure may be a fetal head. The cross-plane images acquired at the first acquisition period may be acquired simultaneously by a single ultrasound device. The cross-plane images acquired at the second subsequent acquisition period may be acquired simultaneously by a single ultrasound device.

20 Claims, 5 Drawing Sheets

(51) Int. Cl.
*A61B 8/08* (2006.01)
*A61B 8/13* (2006.01)

(52) U.S. Cl.
CPC ............ *A61B 8/463* (2013.01); *A61B 8/5223* (2013.01); *G06T 7/0014* (2013.01); *G06T 2207/10136* (2013.01); *G06T 2207/20104* (2013.01); *G06T 2207/30044* (2013.01)

(56) References Cited

U.S. PATENT DOCUMENTS

| | | | |
|---|---|---|---|
| 8,798,342 B2 | 8/2014 | Perrey et al. | |
| 2008/0146932 A1* | 6/2008 | Chalana | A61B 5/204 600/447 |
| 2009/0012432 A1* | 1/2009 | Sharf | A61B 5/0031 600/588 |
| 2009/0093716 A1* | 4/2009 | Deischinger | A61B 8/0866 600/443 |
| 2011/0257529 A1* | 10/2011 | Casciaro | A61B 8/0866 600/443 |
| 2015/0257730 A1* | 9/2015 | Masumoto | A61B 8/0841 600/440 |
| 2016/0074006 A1* | 3/2016 | Patruno | A61B 8/0866 600/443 |

OTHER PUBLICATIONS

Dückelmann et al., "Measurement of fetal head descent using the 'angle of progression' on transperineal ultrasound imaging is reliable regardless of fetal head station or ultrasound expertise," Ultrasound Obstet Gynecol 2010; 35: 216-222.*

Ghi et al., "Diagnosis of station and rotation of the fetal head in the second stage of labor with intrapartum translabial ultrasound," Ultrasound Obstet Gynecol 2009; 33: 331-336.*

* cited by examiner

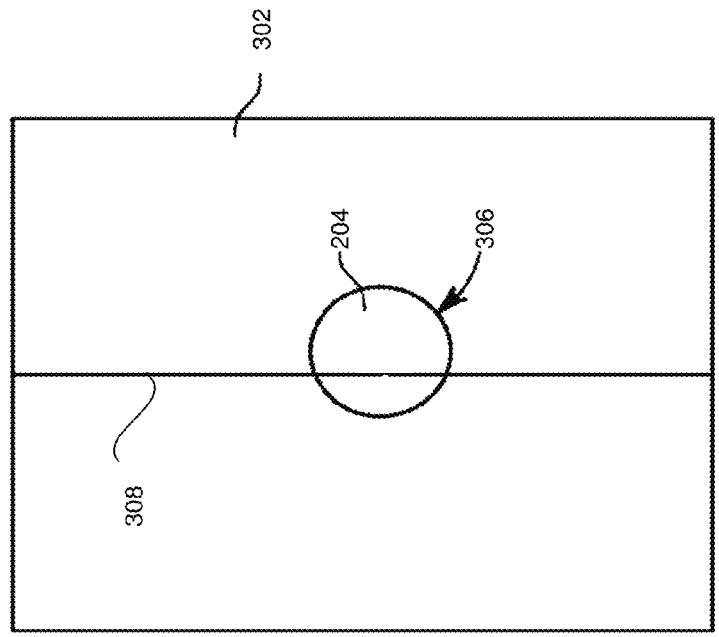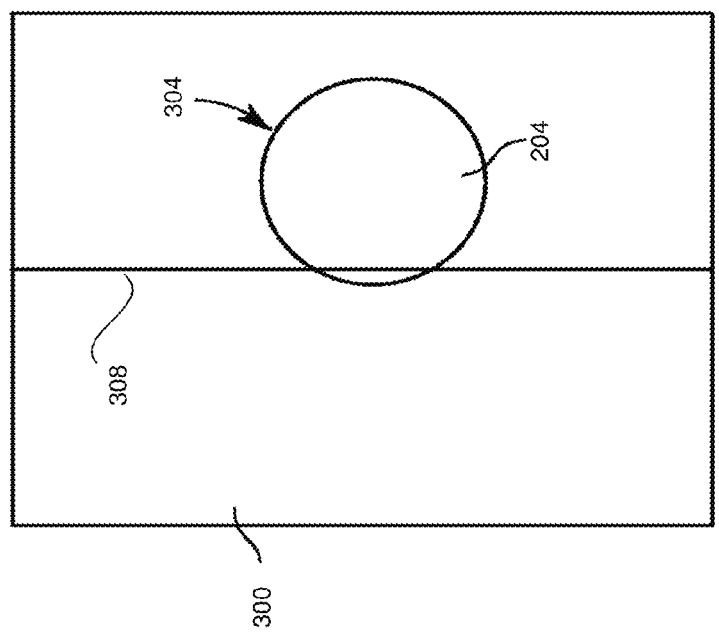
FIG. 3

METHOD AND SYSTEM FOR ENHANCED FETAL VISUALIZATION BY DETECTING AND DISPLAYING A FETAL HEAD POSITION WITH CROSS-PLANE ULTRASOUND IMAGES

FIELD

Certain embodiments of the invention relate to ultrasound imaging. More specifically, certain embodiments of the invention relate to a method and system for enhanced fetal visualization, such as labor progress, by detecting and displaying fetal head positions with cross-plane two-dimensional ultrasound images to determine fetal head rotation.

BACKGROUND

Ultrasound imaging is a medical imaging technique for imaging organs and soft tissues in a human body. Ultrasound imaging uses real time, non-invasive high frequency sound waves to produce a two-dimensional (2D) image and/or a three-dimensional (3D) image.

Ultrasound imaging may be helpful in evaluating the progression of labor and/or other fetal measurements by allowing examination of cervical dilation, fetal presentation, position, rotation, and descent. A prolonged second stage of labor is a type of dystocia, whereby the fetus has not been delivered within three hours in nulliparous women or two hours in multiparous women, after the cervix has become fully dilated. Women undergoing a prolonged second stage of labor typically need intervention, which involves instrumental delivery (using obstetric forceps or ventouse) or Cesarean section or failed instrumental delivery followed by Cesarean section.

In recent years, the rate of Cesarean section has increased dramatically. The failure to progress and fetal distress are the two most common indications for performing surgical deliveries or Cesarean section. Cesarean sections are associated with the risk of maternal morbidities such as bladder trauma and hematoma and unnecessary Cesarean sections are best avoided.

Currently, digital transvaginal examination of fetal descent is typically used to evaluate fetal head station and rotation, but this method is subjective and inaccurate with high interobserver variability. Recent studies have shown that ultrasound imaging might allow objective quantification of the level of fetal head descent in the birth canal. Multiple measurements have been proposed including the fetal head-perineum distance and measuring the 'angle of progression' (AOP) to evaluate the labor progress. With regard to AOP, it has been shown that the greater the AOP in the second stage of labor, the greater the probability of successful assisted or spontaneous delivery. Studies with fetuses in the direct occipitoanterior position have shown that the AOP correlates well with the decision to opt for spontaneous vaginal or instrumental delivery or Cesarean section. Although AOP may constitute a suitable, objective tool to evaluate progress of labor, AOP does not provide information regarding the fetal head rotation, which may also helpful in determining labor progress.

Specifically, as labor progresses, the fetal head rotates in a predictable way to fit through the pelvis. As discussed above, digital transvaginal examination of fetal head rotation can be unreliable. The position of the fetal head within the birth canal may be monitored with two-dimensional (2D) or three-dimensional (3D) ultrasound imaging. It is difficult and error prone, however, to determine the head orientation and/or rotation within a single plane of fetal descent when using 2D ultrasound imaging. Moreover, the use of 3D ultrasound imaging has its own challenges, such as needing a 3D ultrasound probe, having to register the 3D image data, and the ultrasound operator having to manually pick ultrasound slices for evaluation of head rotation (e.g., by determining the eye location), which can be difficult and tedious.

Other efforts for determining fetal head rotation include combining position tracking technology with advanced ultrasound imaging. For example, LABORPRO, which was developed by TRIG MEDICAL, maps the maternal pelvis by manually marking points on the pelvis or using a position sensor. This is followed by marking known fetal head landmarks on the ultrasound image. The two markings enable LABORPRO to determine the spatial position of the fetal head in relation to the pelvic bone, which may be tracked to provide fetal head rotation information. However, setting up and implementing the system in LABORPRO may be difficult in a chaotic atmosphere such as during labor.

Further limitations and disadvantages of conventional and traditional approaches will become apparent to one of skill in the art, through comparison of such systems with some aspects of the present invention as set forth in the remainder of the present application with reference to the drawings.

BRIEF SUMMARY

A system and/or method is provided for enhanced fetal visualization by detecting and displaying fetal head positions with cross-plane two-dimensional ultrasound images to determine fetal head rotation, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

BRIEF DESCRIPTION OF SEVERAL VIEWS OF THE DRAWINGS

FIG. 3 illustrates an exemplary schematic representation of a first cross-plane image and a second cross-plane image, in accordance with an embodiment.

DETAILED DESCRIPTION

Figure 1:
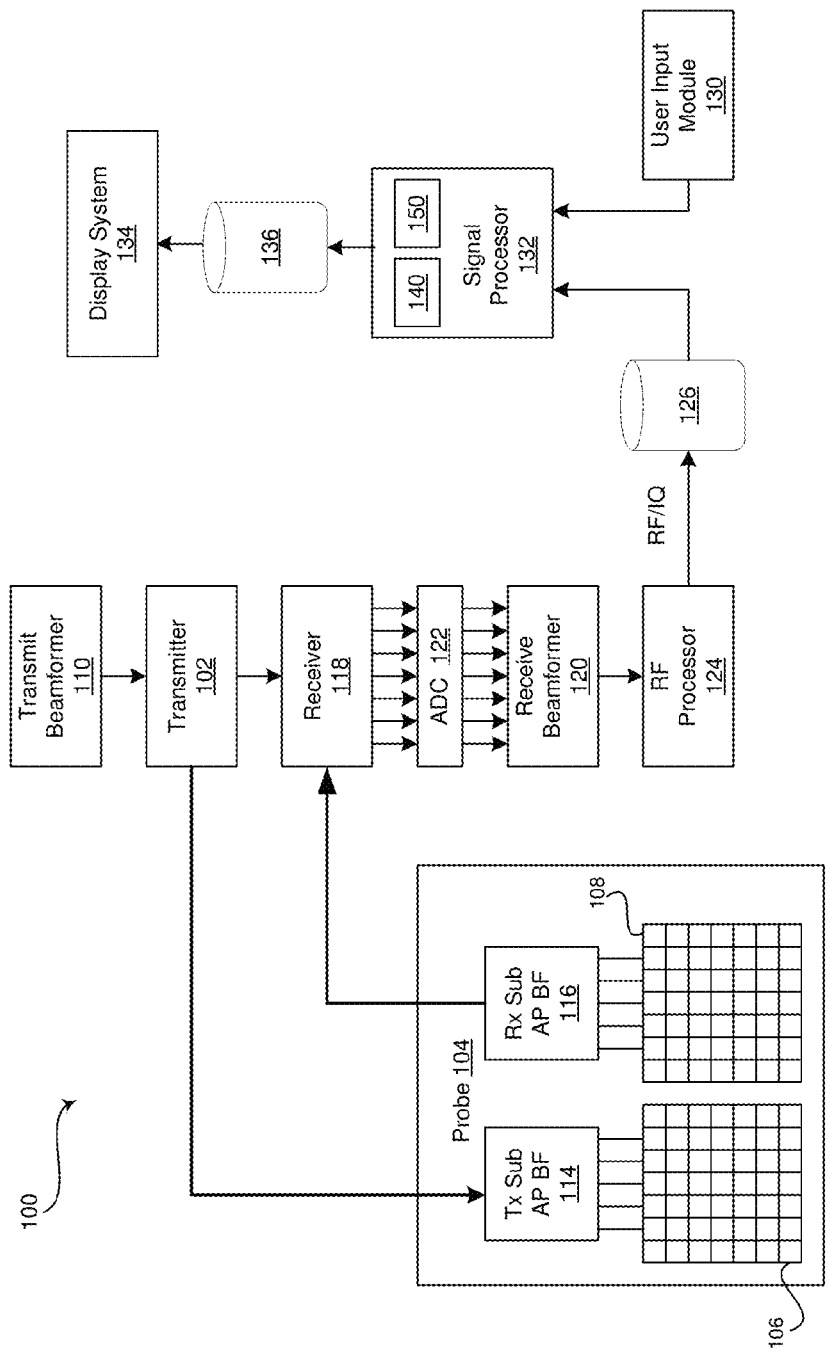
FIG. 1 is a block diagram of an exemplary ultrasound system that is operable to provide fetal visualization by detecting and displaying fetal head positions with cross-plane two-dimensional ultrasound images to determine fetal head rotation, in accordance with an embodiment.

Certain embodiments may be found in a method and system for providing enhanced fetal visualization by detecting and displaying fetal head positions with cross-plane two-dimensional ultrasound images to determine fetal head rotation. For example, various aspects have the technical effect of enhancing visualization of a structure, such as a fetal head, by fitting two-dimensional (2D) cross-plane ultrasound images with a characteristic model, such as ellipses. Moreover, certain embodiments have the technical effect of tracking changes over time, such as periodically during labor and delivery, in the shapes of sets of characteristic models from 2D cross-plane ultrasound images to determine an amount of rotation of the modeled structure. Furthermore, certain embodiments have the technical effect of facilitating analysis of simultaneously acquired 2D cross-plane ultrasound images to provide information regarding an amount of rotation of a fetal head, a current rotational position of the fetal head, and/or labor progress.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an exemplary embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode, CF-mode and/or sub-modes of CF such as TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations needed for the invention, such as single or multi-core: CPU, Graphics Board, DSP, FPGA, ASIC or a combination thereof.

Moreover, although certain embodiments in the foregoing description may describe analyzing the position and rotation of a fetal head, for example, unless so claimed, the scope of various aspects of the present invention should not be limited to a fetal head and may additionally and/or alternatively be applicable to any suitable imaged structure having a changing position and/or rotation.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system that is operable to provide enhanced fetal visualization by detecting and displaying fetal head positions with cross-plane two-dimensional ultrasound images to determine fetal head rotation, in accordance with an embodiment of the invention. Referring to FIG. 1, there is shown an ultrasound system 100. The ultrasound system 100 comprises a transmitter 102, an ultrasound probe 104, a transmit beamformer 110, a receiver 118, a receive beamformer 120, a RF processor 124, a RF/IQ buffer 126, a user input module 130, a signal processor 132, an image buffer 136, and a display system 134.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive and demodulate the signals from the receive sub-aperture beamformer 116. The demodulated analog signals may be communicated to one or more of the plurality of A/D converters 122.

The plurality of A/D converters 122 may comprise suitable logic, circuitry, interfaces and/or code that may be operable to convert the demodulated analog signals from the receiver 118 to corresponding digital signals. The plurality of A/D converters 122 are disposed between the receiver 118 and the receive beamformer 120. Notwithstanding, the invention is not limited in this regard. Accordingly, in some embodiments of the invention, the plurality of A/D converters 122 may be integrated within the receiver 118.

The receive beamformer 120 may comprise suitable logic, circuitry, interfaces and/or code that may be operable to perform digital beamforming processing to, for example, sum the delayed channel signals received from the plurality of A/D converters 122 and output a beam summed signal. The resulting processed information may be converted back to corresponding RF signals. The corresponding output RF signals that are output from the receive beamformer 120 may be communicated to the RF processor 124. In accordance with some embodiments of the invention, the receiver 118, the plurality of A/D converters 122, and the beamformer 120 may be integrated into a single beamformer, which may be digital.

The RF processor 124 may comprise suitable logic, circuitry, interfaces and/or code that may be operable to demodulate the RF signals. In accordance with an embodiment of the invention, the RF processor 124 may comprise a complex demodulator (not shown) that is operable to demodulate the RF signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The user input module 130 may be utilized to input patient data, surgical instrument data, scan parameters, settings, configuration parameters, change scan mode, identify structure in image data, and the like. In an exemplary embodiment of the invention, the user input module 130 may be operable to configure, manage and/or control operation of one or more components and/or modules in the ultrasound system 100. In this regard, the user input module 130 may be operable to configure, manage and/or control operation of transmitter 102, the ultrasound probe 104, the transmit beamformer 110, the receiver 118, the receive beamformer 120, the RF processor 124, the RF/IQ buffer 126, the user input module 130, the signal processor 132, the image buffer 136, and/or the display system 134.

The signal processor 132 may comprise suitable logic, circuitry, interfaces and/or code that may be operable to process ultrasound scan data (i.e., RF signal data or IQ data pairs) for generating cross-plane 2D ultrasound image for presentation on a display system 134. In various embodiments, the cross-plane image data for processing by the signal processor 132 may be acquired simultaneously or consecutively with one ultrasound probe 104. The signal processor 132 is operable to perform one or more processing operations according to a plurality of selectable ultrasound modalities on the acquired ultrasound scan data. In an exemplary embodiment of the invention, the signal processor 132 may be operable to perform compounding, motion tracking, and/or speckle tracking. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation.

The ultrasound system 100 may be operable to continuously acquire ultrasound scan data at a frame rate that is suitable for the imaging situation in question. Typical frame rates range from 20-70 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several seconds' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include an identification module 140 that comprises suitable logic, circuitry, interfaces and/or code that may be operable to process cross-plane 2D ultrasound scan data to identify a fetal head in each of the acquired cross-plane images and apply a characteristic model to the fetal head in each of the cross-plane images. The cross-plane images fit with the characteristic model may be provided to the image buffer 136 and/or the display system 134. The characteristic model may be, for example, an ellipse or any suitable shape corresponding with the identified structure. The identification module 140 may receive an instruction from user input module 130 for manually positioning the characteristic model over the fetal head in the cross-plane images. Additionally and/or alternatively, the identification module 140 may apply image detection techniques and/or algorithms to automatically and/or semi-automatically identify the fetal head in each of the cross-plane images. The image detection techniques and/or algorithms may search the image data for structure corresponding with the fetal head. The search may be based on known or learned structure and/or positional information. For example, the image detection techniques and/or algorithms may access information from related processed image data or other stored information regarding the position of the fetal head, the pubic bone, and/or the relationship between the pubic bone and the fetal head. Additionally and/or alternatively, the identification module 140 may be provided with user input information at the user input module 130 identifying a region or structure, such as the fetal head, pubic bone, and/or portions thereof. The identification module 140 may be operable to fit the 2D cross-plane images with a characteristic model based on the identification of the fetal head.

In various embodiments, the identification module 140 may attempt to identify the fetal head automatically and apply a characteristic model to the automatically identified fetal head. The identification module 140 may display the automatically identified fetal head with the overlaid or superimposed characteristic model in the cross-plane images at the display system 134. If the fetal head cannot be automatically identified or if the placement of the characteristic model is not satisfactory to a user, the user may select and/or be prompted to select a region or structure in the displayed 2D cross-plane images to assist the identification module 140 in performing a semi-automatic search of the cross-plane 2D images based on the region and/or structure selected using the user input module 130. Additionally and/or alternatively, the identification module 140 may prompt a user for assistance at the onset prior to attempting to identify the fetal head and fitting each of the cross-plane images with the characteristic model.

As used herein, the term "manually" refers to the exemplary embodiments where a user identifies the entire fetal head to position the characteristic model using the user input module 130. As used herein, the term "semi-automatically" refers to the exemplary embodiments where a user provides assistance to the fetal head identification module 140 by identifying a region or structure in the image data for the fetal head identification module 140 to apply its image detection techniques and/or algorithms. The fetal head identification module 140 may then identify the fetal head in the cross-plane images and position the characteristic model based on the identification. As used herein, the term "automatically" in the context of the fetal head identification module 140 refers to the exemplary embodiments where the fetal head identification module 140 identifies the fetal head and positions the characteristic model in the cross-plane images without user assistance.

The signal processor 132 may include a measurement module 150 that comprises suitable logic, circuitry, interfaces and/or code that may be operable to compute measurements corresponding with a fetus. For example, the measurement may relate to a determination of an amount of rotation of a fetal head, a determination of a current fetal head rotational position, a progress of delivery, a fetal head-perineum distance measurement, an "angle of progression" (AOP) measurement, a distance of progression measurement, a head direction measurement, a biparietal diameter (BPD), a head circumference, an abdominal circumference, a humerus length, a femur length, or any suitable fetal measurement. The measurement may be computed automatically based on the ultrasound scan data acquired by the ultrasound probe 104 and/or manually based on the ultrasound scan data and user input received from the user input module 130, for example. The fetal measurement is displayed for interpretation at display system 134.

Figure 2:
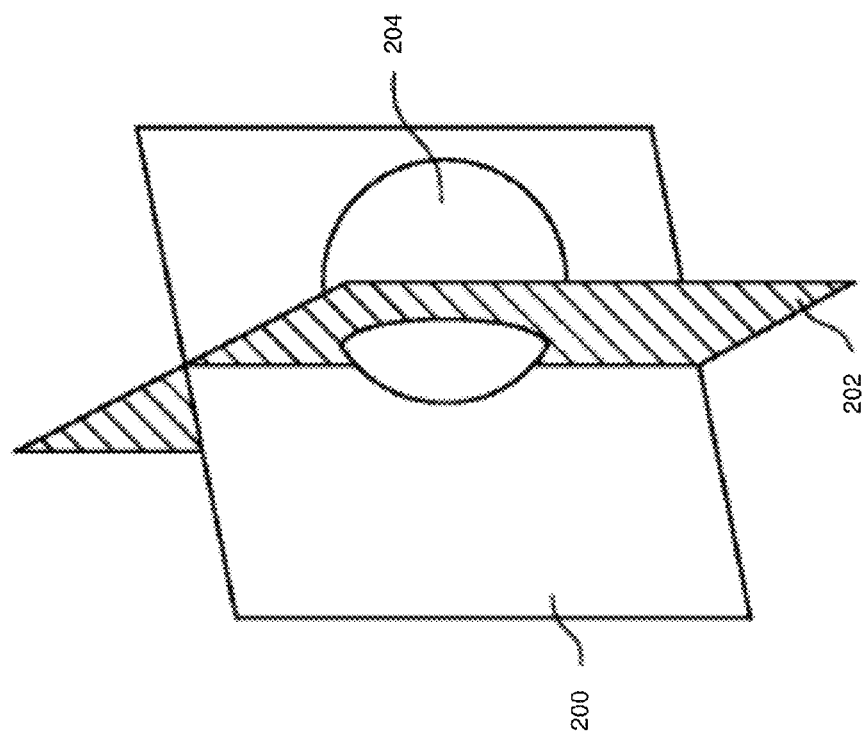
FIG. 2 illustrates an exemplary schematic representation of a first plane and a second plane intersecting a structure, in accordance with an embodiment.

FIG. 2 illustrates an exemplary schematic representation of a first plane 200 and a second plane 202 intersecting a structure 204, in accordance with an embodiment. Referring to FIG. 2, the first 200 and second 202 planes are perpendicular to each other. The structure 204 may be a fetal head, for example, or any suitable structure. The 2D ultrasound image data acquired of the first plane 200 may be displayed as a first cross-plane image and the 2D ultrasound image data acquired of the second plane 202 may be displayed as a second cross-plane image as described below in reference to FIG. 3, for example.

FIG. 3 illustrates an exemplary schematic representation of a first cross-plane image 300 and a second cross-plane image 302, in accordance with an embodiment. Referring to FIG. 3, a first cross-plane image 300 illustrating a first contour 304 of a structure 204 and a second cross-plane image 302 illustrating a second contour 306 of the structure 204 is shown. In various embodiments, the first 300 and second 400 cross-plane images may be generated by the signal processor 132 from 2D ultrasound image data acquired simultaneously or consecutively with one ultrasound probe 104. The first 300 and second 302 cross-plane images may be presented at the display system 134 and/or stored in image buffer 136. The first cross-plane image 300 may represent a 2D ultrasound image of the first plane 200 (shown in FIG. 2) and the second cross-plane image 302 may represent a 2D ultrasound image of the second plane 202 (shown in FIG. 2). The first 300 and second 302 cross-plane images may be perpendicular to each other and intersect at line 308. In various embodiments, intersecting line 308 is not displayed in the cross-plane images 300, 302. A common reference number is used to identify the structure 204 in both FIGS. 2 and 3 in accordance with an embodiment. In various embodiments, the structure 204 may be a fetal head or any suitable structure.

Figure 4:
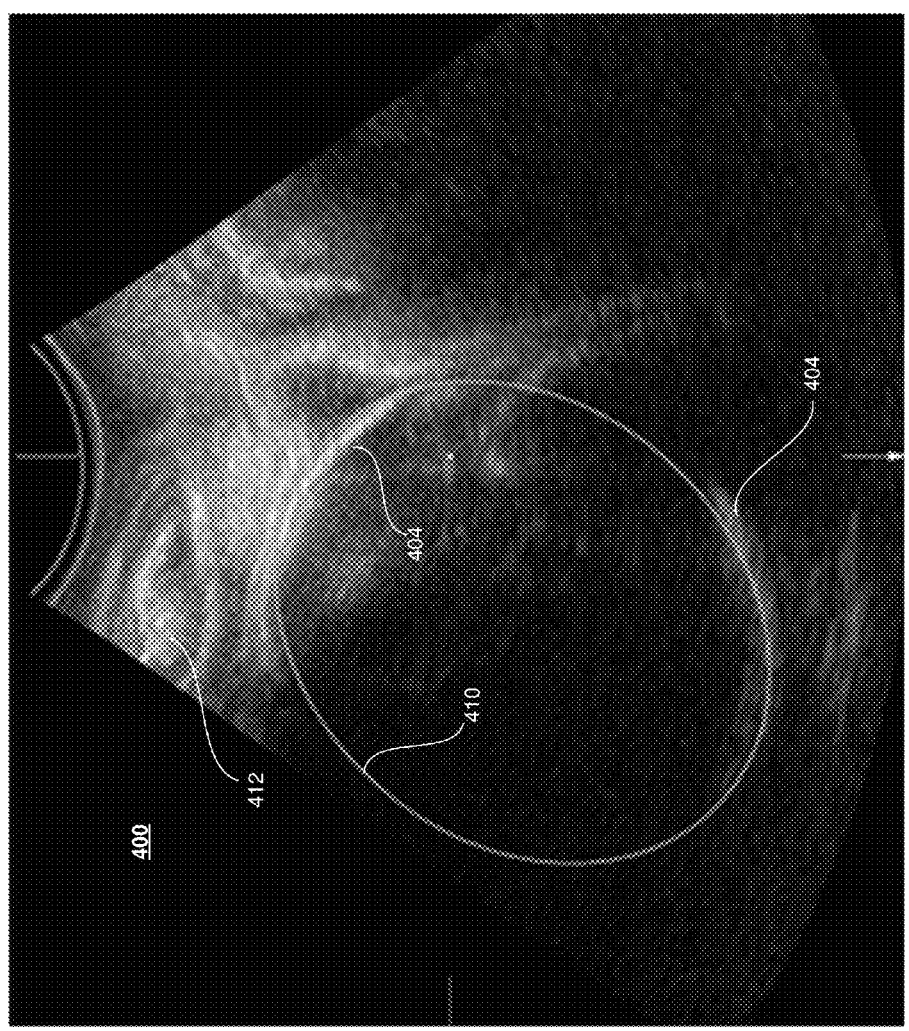
FIG. 4 illustrates an exemplary first cross-plane ultrasound image fitted with a first characteristic model, in accordance with an embodiment.

FIG. 4 illustrates an exemplary first cross-plane ultrasound image 400 fitted with a first characteristic model 410, in accordance with an embodiment. Referring to FIG. 4, the first cross-plane image 400 comprises pubic bone structure 412 and fetal head structure 404. The fetal head structure 404 is fit with a characteristic model 410 to identify the fetal head 404 in the 2D ultrasound image data. The characteristic model 410 may be an ellipse or any suitable shape that corresponds with the identified structure 404. The characteristic model 410 may be positioned over the fetal head 404 manually using a user input module 130 or the identification module 140 may automatically and/or semi-automatically identify the fetal head structure 404 and fit the identified structure 404 with the characteristic model 410. For example, the identification module 140 may apply image detection techniques and/or algorithms to identify structure, such as the pubic bone 412 and fetal head 404, so the characteristic model 410 may be overlaid or superimposed at the appropriate position on the first cross-plane ultrasound image 400. The identification module 140 or user input module 130 may similarly identify the fetal head structure 404 in a second cross-plane image that is perpendicular to the first cross-plane image 400. The set of characteristic models 410 may form a shape that can be analyzed with prior or subsequently acquired sets of characteristic models 410 by the measurement module 150 to calculate an amount of rotation of a fetal head, a determination of a current fetal head rotational position, a progress of delivery, or any suitable measurement.

Still referring to FIG. 4, the first cross-plane ultrasound image 400 may be generated by the signal processor 132 from 2D ultrasound image data acquired with an ultrasound probe 104. In various embodiments, the ultrasound probe 104 may simultaneously or consecutively acquire a second cross-plane ultrasound image perpendicular to the first cross-plane ultrasound image 400. The first cross-plane ultrasound image 400 may be presented with the second cross-plane ultrasound image at the display system 134 and/or may be stored in the image buffer 136. The first cross-plane ultrasound image 400 may correspond with the first cross-plane image 300 (shown in FIG. 3) that represents a 2D image of the first plane 200 (shown in FIG. 2).

Figure 5:
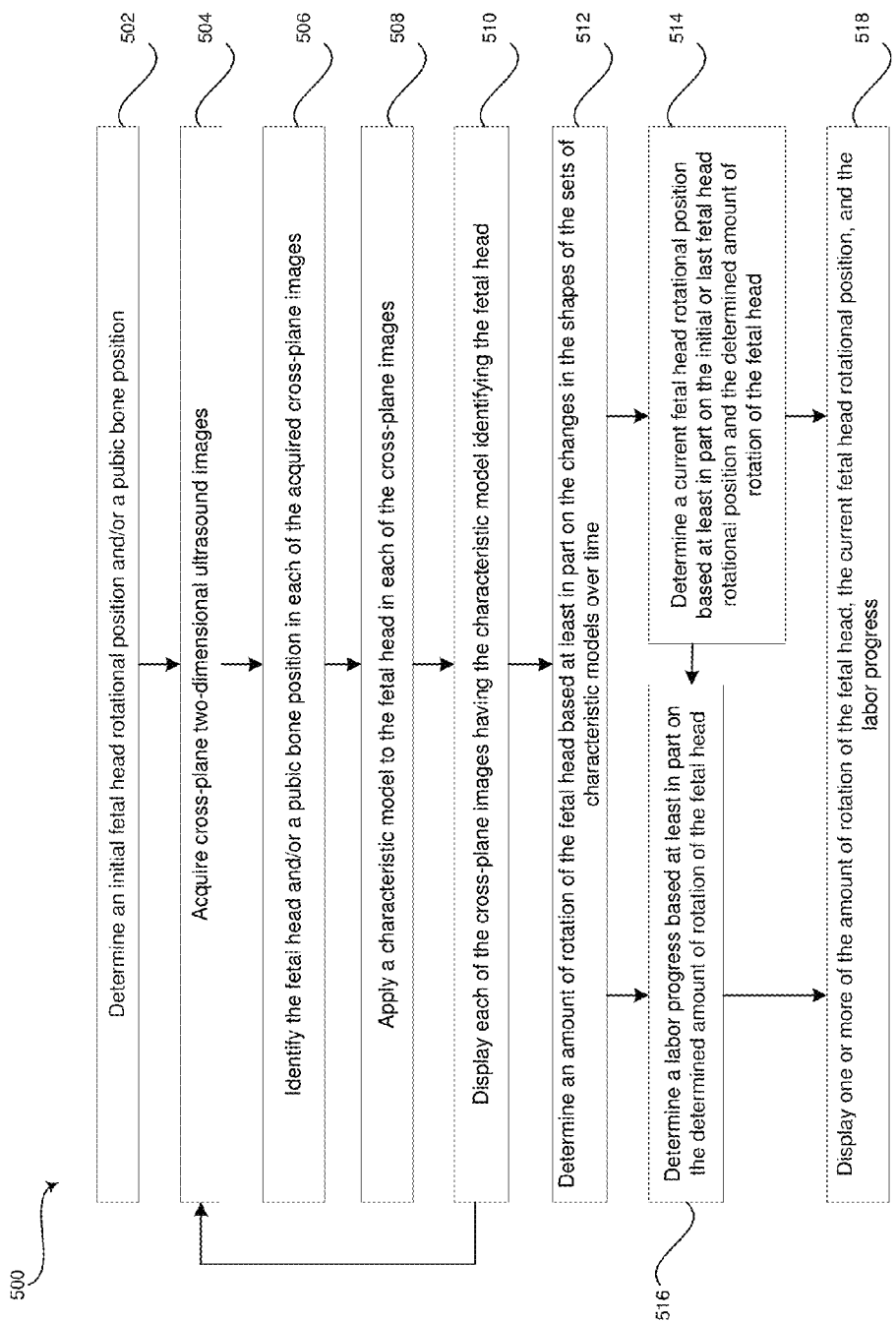
FIG. 5 is a flow chart illustrating exemplary steps that may be utilized for providing enhanced fetal visualization by detecting and displaying fetal head positions with cross-plane two-dimensional ultrasound images to determine fetal head rotation, in accordance with an embodiment.

FIG. 5 is a flow chart 500 illustrating exemplary steps 502-518 that may be utilized for providing enhanced fetal visualization by detecting and displaying fetal head positions with cross-plane two-dimensional ultrasound images 300, 302, 400 to determine fetal head rotation, in accordance with an embodiment. Referring to FIG. 5, there is shown a flow chart 500 comprising exemplary steps 502 through 518. Certain embodiments of the present invention may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

In step 502, the signal processor 132 may determine an initial fetal head 404 rotational position and/or a pubic bone 412 position. For example, an ultrasound system 100 may acquire ultrasound data 400 as described above with regard to FIG. 1. The signal processor 132 may perform image detection techniques and/or algorithms to automatically and/or semi-automatically identify a fetal head 404 rotational position and/or a pubic bone 412 position. The signal processor 132 may locate the fetal head 404 and identify orbital bone and/or nasal bone structure, for example, to determine the orientation of the fetal head 404. Additionally and/or alternatively, the signal processor 132 may receive information from a user input module 130 manually identifying the orientation of the fetal head 404 in the ultrasound image data 400. For example, an ultrasound operator may use the user input module 130 to manually position a characteristic model 410 with a long axis pointing to twelve o'clock. The initial fetal head rotational position may be used by the measurement module 150, for example, to determine an amount of rotation of the fetal head 404 at step 512 and/or to determine a current fetal head rotation position at step 514 with reference to subsequently acquired and analyzed cross-plane 2D ultrasound images 400. The fetal head 404 position and/or pubic bone 412 position may be used by the identification module 140 of the signal processor 132 to identify the fetal head 404 and/or a pubic bone 412 position in each of the acquired cross-plane images 400 at step 506, for example. In various embodiments, step 502 may be omitted if, for example, the ultrasound operator does not intend for the initial fetal head 404 position and/or pubic bone 412 position to be used to identify the fetal head at step 506 and/or to determine the current fetal head rotational position at step 514.

In step 504, the ultrasound system 100 may acquire cross-plane 2D ultrasound images. The ultrasound system 100 may acquire ultrasound data 400, for example, as described above with regard to FIG. 1. The cross-plane 2D ultrasound image data comprises a first cross-plane ultrasound image 400 and a second cross-plane ultrasound image. The first 400 and second cross-plane ultrasound images may be generated by the signal processor 132 from 2D ultrasound image data acquired simultaneously or consecutively with an ultrasound probe 104. The first cross-plane ultrasound image 400 may be perpendicular to the second cross-plane ultrasound image. The first cross-plane ultrasound image 400 may be presented with the second cross-plane ultrasound image at the display system 134 and/or may be stored in the image buffer 136. The first cross-plane ultrasound image 400 may correspond with the first cross-plane image 300 (shown in FIG. 3) that represents a 2D image of the first plane 200 (shown in FIG. 2). The second cross-plane ultrasound image may correspond with the second cross-plane image 302 (shown in FIG. 3) that represents a 2D image of the second plane 202 (shown in FIG. 2). In various embodiments, the cross-plane images may be acquired during labor and delivery and may illustrate at least a portion of a fetus to provide information for determining labor progress.

In step 506, the identification module 140 of the signal processor 132 may identify a fetal head 404 and/or pubic bone 412 in each of the acquired cross-plane images 300, 302, 400. For example, the identification module 140 may apply image detection techniques and/or algorithms to automatically and/or semi-automatically identify the fetal head in each of the cross-plane images 300, 302, 400 acquired at step 504. The image detection techniques and/or algorithms may search the image data for structure, such as contours 304, 306, corresponding with the fetal head 404. The search may be based on known or learned structure and/or positional information. For example, the image detection techniques and/or algorithms may use the initial fetal head 404 and/or pubic bone 412 positional and/or characteristic information determined at step 502 or from a previous iteration of step 506 to search for the fetal head 404 and/or pubic bone 412 in each of the acquired cross-plane images 300, 302, 400. Moreover, the identification module 140 may be provided with user input information at the user input module 130 identifying a region or structure, such as all or portions of the fetal head 404, pubic bone 412, and the like.

In step 508, a user input module 130 and/or the identification module 140 of the signal processor 132 may apply a characteristic model 410 to the fetal head 404 identified in step 506 in each of the cross-plane images 300, 302, 400. The characteristic model 410 may be an ellipse or any suitable shape that is characteristic of the fitted structure (e.g., a fetal head). The user input module 130 and/or identification module 140 may superimpose or overlay the characteristic model 410 on the identified fetal head structure 404 in each of the cross-plane images 300, 302, 400. For example, the user input module 130 may receive a user input to draw a characteristic model 410 or move a characteristic model 410 into an appropriate position over the identified fetal head 404. Additionally and/or alternatively, the identification module 140 may automatically and/or semi-automatically position the characteristic model 410 in the appropriate position. In an exemplary embodiment, a prompt may be presented at a display system 134 to accept the manually, semi-automatically, and/or automatically positioned characteristic model 410 in each of the cross-plane images 300, 302, 400. In various embodiments, the set of characteristic models 410 identifying the fetal head 404 in the cross-plane images 300, 302, 400 may form a shape that may be tracked over time to determine an amount of rotation as described below with respect to step 512.

In step 510, the identification module 140 of the signal processor 132 may display each of the cross-plane images 300, 302, 400 having the characteristic model 410 identifying the fetal head 404 at the display system 134. For example, the cross-plane images 300, 302, 400 may be displayed side-by-side, above-and-below, on separate selectable pages of a display, and/or on separate monitors of the display system 134, among other things. Additionally and/or alternatively, the cross-plane images 300, 302, 400 may be presented with prior or subsequently acquired and processed cross-plane images 300, 302, 400 to show changes in the shape of the sets of characteristic models that is representative of fetal head rotation.

In various embodiments, steps 504 through 510 may be repeated periodically over time, such as over the course of labor and delivery. In an exemplary embodiment, each iteration of acquiring (step 504), processing (steps 506 and 508), and displaying (step 510) the cross-plane images 300, 302, 400 at steps 504 through 510 may dynamically update the computed and displayed measurements performed at steps 512 through 518.

In step 512, the measurement module 150 of the signal processor 132 may determine an amount of rotation of the fetal head 404 based at least in part on the changes in the shapes of the sets of characteristic models 410 over time. For example, the measurement module 150 may identify a first set of characteristic models 410 representing an image acquisition at a first acquisition period and a second set of characteristic models 410 representing an image acquisition at a second subsequent acquisition period. The first acquisition period corresponds with the time period for acquiring a first set of cross-plane images, either simultaneously or consecutively. The second subsequent acquisition period refers to the time period for acquiring the second set of cross-plane images. The measurement module 150 may compare the shape of the identified first set of characteristic models 410 with the shape of the second set of characteristic models 410. Additionally and/or alternatively, the measurement module 150 may compare the shape of the characteristic models 140 to the initial reference position determined at step 502, for example. A lack of change to the shape of the sets of characteristic models may indicate a lack of rotation, for example. The presence or lack of rotation may assist a doctor in determining whether labor is progressing and/or the rate at which the labor is progressing. In various embodiments, the measurement module 150 may apply one or more algorithms to calculate a distance or degree of rotation based at least in part on the change of shape between sets of characteristic models 410. In an exemplary embodiment, the measurement module 150 may generate a graphical representation illustrating the rotational change of the fetal head 404 for presentation at the display system 134.

In step 514, the measurement module 150 of the signal processor 132 may determine a current fetal head rotational position based at least in part on the initial or last fetal head rotational position and the determined amount of rotation of the fetal head 404. For example, the measurement module 150 may access stored information regarding a previous rotational position of the fetal head 404, such as the initial fetal head position determined at step 502 or the fetal head position determined at step 514 after a previous iteration of steps 504 through 512. The measurement module 150 may apply one or more algorithms to add the amount of rotation of the fetal head 404 calculated at step 512 to the previous rotational position of the fetal head 404 to compute the current fetal head rotational position.

In step 516, the measurement module 150 of the signal processor 132 may determine a labor progress based at least in part on the determined amount of rotation of the fetal head 404. For example, as labor progresses, the fetal head 404 rotates in a predictable way to fit through the pelvis. The measurement module 150 may apply an algorithm correlating these known positions and rotations of the fetal head 404 with the current fetal head rotational position determined at step 514 and/or the amount of rotation of the fetal head 404 determined at step 512 to compute the labor progress. The labor progress may be presented at a display system 134 as a progress bar, a graphical representation illustrating the progress of the labor, a numerical value such as a percentage, and/or any suitable mechanism.

In step 518, the measurement module 150 of the signal processor 132 may display the amount of rotation (determined at step 512), the current fetal head rotational position (determined at step 514), and/or the labor progress (determined at step 516) at the display system 134. For example, the measurement module 150 may present numerical values, graphical representations, and the like, at the display system 134. The one or more measurements may provide a doctor with information related to the labor and delivery progress. In various embodiments, the one or more numerical values, graphical representations, and the like may be presented, for example, with the cross-plane images 300, 302, 400.

Aspects of the present invention provide a method 500 and system 100 for providing enhanced fetal visualization by detecting and displaying fetal head 404 positions with cross-plane two-dimensional ultrasound images 300, 302, 400 to determine fetal head rotation. In accordance with various embodiments of the invention, the method 500 comprises identifying 512, by a processor 132, 150, a first set of characteristic models 410 of the structure 404 in cross-plane images 300, 302, 400 acquired at a first acquisition period. The method 500 comprises identifying 512, by the processor 132, 150, a second set of characteristic models 410 of the structure 404 in cross-plane images 300, 302, 400 acquired at a second subsequent acquisition period. The method 500 comprises determining 512, by the processor 132, 150, the amount of rotation of the structure 404 based at least in part on a difference in shape of the first set of characteristic models 410 and the second set of characteristic models 410.

In various embodiments, the method 500 comprises acquiring 504, by an ultrasound device 100, the cross-plane images 300, 302, 400. The method 500 comprises identifying 506 the structure 404 in each of the acquired cross-plane images 300, 302, 400. The method 500 comprises applying 508 a characteristic model 410 to the identified structure 404 in each of the cross-plane images 300, 302, 400. In certain embodiments, the method 500 comprises determining 516 a labor progress based at least in part on the determined amount of rotation of the structure 404. The structure is a fetal head 404.

In a representative embodiment, the method 500 comprises determining 514 a rotational position of the structure 404 corresponding with the second set of characteristic models 410 based at least in part on the rotational position of the structure 404 corresponding with the first set of characteristic models 410 and the determined amount of rotation of the structure 404. In various embodiments, the method 500 comprises determining 502 an initial rotational position of the structure 404. The method 500 comprises one or more of determining 512, by the processor 132, 150, the amount of rotation of the structure 404 based at least in part on the initial rotational position of the structure 404 and the first set of characteristic models 410, and determining 514 a rotational position of the structure 404 corresponding with the first set of characteristic models 410 based at least in part on the initial rotational position of the structure 404 and the determined amount of rotation of the structure 404.

In certain embodiments, the structure 404 is identified and the characteristic model 410 is applied by one or more of a user input device 130 and the processor 132, 140. In a representative embodiment, the cross-plane images 300, 302, 400 acquired at the first acquisition period are simultaneously acquired by a single ultrasound device 100, 104. The cross-plane images 300, 302, 400 acquired at the second subsequent acquisition period are simultaneously acquired by the single ultrasound device 100, 104. In various embodiments, the method 500 comprises displaying 510 each of the cross-plane images 300, 302, 400 having the characteristic model 410 at a display system 134. The method 500 comprises displaying 518 the determined amount of rotation of the structure 404 at the display system 134. In certain embodiments, the amount of rotation is one or more of a numerical value and a graphical representation.

Various embodiments provide a system 100 for determining an amount of rotation of a structure 404. The system 100 comprises a processor 132, 150 configured to identify a first set of characteristic models 410 of the structure 404 in cross-plane images 300, 302, 400 acquired at a first acquisition period. The processor 132, 150 is configured to identify a second set of characteristic models 410 of the structure 404 in cross-plane images 300, 302, 400 acquired at a second subsequent acquisition period. The processor 132, 150 is configured to determine the amount of rotation of the structure 404 based at least in part on a difference in shape of the first set of characteristic models 410 and the second set of characteristic models 410.

In a representative embodiment, the system 100 comprises a single ultrasound device 100, 104 operable to simultaneously acquire the cross-plane images 300, 302, 400 acquired at the first acquisition period. The single ultrasound device 100, 104 is operable to simultaneously acquire the cross-plane images 300, 302, 400 acquired at the second subsequent acquisition period. In certain embodiments, the system comprises a user input device 130. In various embodiments, one or more of the user input device 130 and the processor 132, 140 is configured to identify the structure 404 in each of the acquired cross-plane images 300, 302, 400. The one or more of the user input device 130 and the processor 132, 140 is configured to apply a characteristic model 410 to the identified structure 404 in each of the cross-plane images 300, 302, 400. In a representative embodiment, the processor 132, 150 is configured to determine a labor progress based at least in part on the determined amount of rotation of the structure 404. The structure is a fetal head 404.

In certain embodiments, the system 100 comprises a display system 134 configured to display each of the cross-plane images 300, 302, 400 having the characteristic model 410 and the determined amount of rotation of the structure 404. The amount of rotation is one or more of a numerical value and a graphical representation. In various embodiments, the processor 132, 150 is configured to determine a rotational position of the structure 404 corresponding with the second set of characteristic models 410 based at least in part on the rotational position of the structure 404 corresponding with the first set of characteristic models 410 and the determined amount of rotation of the structure 404. In a representative embodiment, the processor 132 is configured to determine an initial rotational position of the structure 404. The processor 132, 150 is configured to one or more of determine the amount of rotation of the structure 404 based at least in part on the initial rotational position of the structure 404 and the first set of characteristic models 410, and determine a rotational position of the structure 404 corresponding with the first set of characteristic models 410 based at least in part on the initial rotational position of the structure 404 and the determined amount of rotation of the structure 404.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments of the invention may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for providing enhanced fetal visualization by detecting and displaying fetal head positions with cross-plane two-dimensional ultrasound images to determine fetal head rotation.

Accordingly, the present invention may be realized in hardware, software, or a combination of hardware and software. The present invention may be realized in a centralized fashion in at least one computer system, or in a distributed fashion where different elements are spread across several interconnected computer systems. Any kind of computer system or other apparatus adapted for carrying out the methods described herein is suited.

The present invention may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method for determining an amount of rotation of a structure, the method comprising:
   acquiring, by an ultrasound device, two-dimensional intersecting cross-plane images at a first acquisition period and at a second subsequent acquisition period;
   identifying, by a processor communicatively coupled to the ultrasound device, a first set of characteristic models forming a shape of the structure in the two-dimensional intersecting cross-plane images acquired at the first acquisition period;
   identifying, by the processor, a second set of characteristic models forming a shape of the structure in the two-dimensional intersecting cross-plane images acquired at the second subsequent acquisition period;
   determining, by the processor, the amount of rotation of the structure based at least in part on a difference in the shape of the first set of characteristic models and the shape of the second set of characteristic models; and
   presenting, at a display system, the determined amount of rotation of the structure.

2. The method according to claim 1, comprising:
   identifying the structure in each of the acquired two-dimensional intersecting cross-plane images; and
   applying a distinct characteristic model to the identified structure in each of the two-dimensional intersecting cross-plane images.

3. The method according to claim 1, comprising determining a labor progress based at least in part on the determined amount of rotation of the structure, wherein the structure is a fetal head.

4. The method according to claim 1, comprising determining a rotational position of the structure corresponding with the second set of characteristic models based at least in part on a rotational position of the structure corresponding with the first set of characteristic models and the determined amount of rotation of the structure.

5. The method according to claim 1, comprising:
determining an initial rotational position of the structure; and
one or more of:
   determining, by the processor, the amount of rotation of the structure based at least in part on the initial rotational position of the structure and the first set of characteristic models, and
   determining a rotational position of the structure corresponding with the first set of characteristic models based at least in part on the initial rotational position of the structure and the determined amount of rotation of the structure.

6. The method according to claim 2, wherein the structure is identified and the distinct characteristic model is applied by one or more of a user input device and the processor.

7. The method according to claim 2, wherein the ultrasound device is a single ultrasound device, wherein the two-dimensional intersecting cross-plane images acquired at the first acquisition period are simultaneously acquired by the single ultrasound device, and wherein the two-dimensional intersecting cross-plane images acquired at the second subsequent acquisition period are simultaneously acquired by the single ultrasound device.

8. The method according to claim 2, comprising displaying each of the two-dimensional intersecting cross-plane images having the distinct characteristic model at the display system.

9. The method according to claim 1, wherein the determined amount of rotation of the structure presented at the display system is one or more of a numerical value and a graphical representation.

10. A system for determining an amount of rotation of a structure, the system comprising:
an ultrasound device configured to acquire two-dimensional intersecting cross-plane images at a first acquisition period and at a second subsequent acquisition period;
a processor communicatively coupled to the ultrasound device and configured to:
   identify a first set of characteristic models forming a shape of the structure in the two-dimensional intersecting cross-plane images acquired at the first acquisition period;
   identify a second set of characteristic models forming a shape of the structure in the two-dimensional intersecting cross-plane images acquired at the second subsequent acquisition period; and
   determine the amount of rotation of the structure based at least in part on a difference in the shape of the first set of characteristic models and the shape of the second set of characteristic models; and
a display system configured to present the determined amount of rotation of the structure.

11. The system according to claim 10, wherein the ultrasound device is a single ultrasound device operable to:
simultaneously acquire the two-dimensional cross-plane images acquired at the first acquisition period, and
simultaneously acquire the two-dimensional cross-plane images acquired at the second subsequent acquisition period.

12. The system according to claim 10, comprising a user input device, and wherein one or more of the user input device and the processor is configured to:
   identify the structure in each of the acquired two-dimensional intersecting cross-plane images, and
   apply a distinct characteristic model to the identified structure in each of the two-dimensional intersecting cross-plane images.

13. The system according to claim 10, wherein the processor is configured to determine a labor progress based at least in part on the determined amount of rotation of the structure, and wherein the structure is a fetal head.

14. The system according to claim 10, wherein the display system is configured to display each of the two-dimensional intersecting cross-plane images having the distinct characteristic model, wherein the amount of rotation is one or more of a numerical value and a graphical representation.

15. The system according to claim 10, wherein the processor is configured to determine a rotational position of the structure corresponding with the second set of characteristic models based at least in part on a rotational position of the structure corresponding with the first set of characteristic models and the determined amount of rotation of the structure.

16. The system according to claim 10, wherein the processor is configured to:
determine an initial rotational position of the structure; and
one or more of:
   determine the amount of rotation of the structure based at least in part on the initial rotational position of the structure and the first set of characteristic models, and
   determine a rotational position of the structure corresponding with the first set of characteristic models based at least in part on the initial rotational position of the structure and the determined amount of rotation of the structure.

17. A non-transitory computer readable medium having stored thereon, a computer program having at least one code section, the at least one code section being executable by a machine for causing the machine to perform steps comprising:
receiving, from an ultrasound device, two-dimensional intersecting cross-plane images at a first acquisition period and at a second subsequent acquisition period;
identifying a first set of characteristic models forming a shape of the structure in the two-dimensional intersecting cross-plane images acquired at the first acquisition period;
identifying a second set of characteristic models forming a shape of the structure in the two-dimensional intersecting cross-plane images acquired at the second subsequent acquisition period;
determining the amount of rotation of the structure based at least in part on a difference in the shape of the first set of characteristic models and the shape of the second set of characteristic models; and
presenting the determined amount of rotation of the structure at a display system.

18. The non-transitory computer readable medium according to claim 17, comprising:
identifying the structure in each of the acquired two-dimensional intersecting cross-plane images; and
applying a distinct characteristic model to the identified structure in each of the two-dimensional intersecting cross-plane images.

19. The non-transitory computer readable medium according to claim 17, comprising determining a labor progress based at least in part on the determined amount of rotation of the structure, wherein the structure is a fetal head.

20. The non-transitory computer readable medium according to claim 17, comprising displaying each of the two-dimensional intersecting cross-plane images having the distinct characteristic model at the display system, wherein the amount of rotation is one or more of a numerical value and a graphical representation.

* * * * *